United States Patent [19]

Peters et al.

[11] Patent Number: 4,647,450

[45] Date of Patent: Mar. 3, 1987

[54] CHEWING GUM COMPOSITIONS CONTAINING MAGNESIUM TRISILICATE ABSORBATES

[75] Inventors: David Peters, Long Valley; John Denick, Jr., Newton; Anil K. Talwar, Long Valley, all of N.J.

[73] Assignee: Warner-Lambert Company, Morris Plains, N.J.

[21] Appl. No.: 811,083

[22] Filed: Dec. 19, 1985

Related U.S. Application Data

[63] Continuation-in-part of Ser. No. 516,002, Jul. 20, 1983, Pat. No. 4,581,232.

[51] Int. Cl.$^4$ ............................ A61K 9/68; A61K 9/18
[52] U.S. Cl. ........................................ 424/48; 424/155
[58] Field of Search ................................... 424/48, 155

[56] References Cited

U.S. PATENT DOCUMENTS

| | | | |
|---|---|---|---|
| 2,881,113 | 4/1959 | Millman | 424/155 |
| 3,337,402 | 8/1967 | Zentner | 424/155 |
| 3,352,752 | 11/1967 | Puetzer et al. | 424/155 |
| 3,432,593 | 3/1969 | Shepard | 424/20 |
| 3,449,266 | 6/1969 | Cashman et al. | 252/522 |
| 3,567,819 | 3/1971 | Idson et al. | 424/155 |
| 3,636,200 | 1/1972 | Zentner | 424/155 |
| 4,029,797 | 6/1977 | Bianculli | 424/260 |
| 4,401,674 | 8/1983 | Dowrick | 424/211 |

FOREIGN PATENT DOCUMENTS 1578541  7/1977  United Kingdom .

OTHER PUBLICATIONS

Khalil, et al., C.A. 79:9826n (1973).
Magid, et al., C.A. 57:12649b (1962).
Zentner, C.A. 65:578a (1966).
Couchoud, et al., C.A. 78:140400r (1973).
El-Nakeeb, et al., C.A. 68:89857j (1968).
El Masry, et al., C.A. 81:41376t (1974).

*Primary Examiner*—Shep K. Rose
*Attorney, Agent, or Firm*—Charles A. Gaglia, Jr.; Gary M. Nath

[57] ABSTRACT

A chewing gum composition containing a magnesium trisilicate having a surface area of at least 400 m$^2$/g and having a flake-like structure with multiple interstitial spaces, and having adsorbed therein from about 1% to about 20% by weight of the adsorbate of a medicament drug. Such compositions may be in the form of sticks, slabs, chunks, balls, ropes, shredded tablets and/or center filled.

1 Claim, 4 Drawing Figures

CHEWING GUM COMPOSITIONS CONTAINING MAGNESIUM TRISILICATE ABSORBATES

This is a continuation-in-part of copending U.S. application Ser. No. 516,002 filed July 20, 1983, now U.S. 4,581,232.

This invention relates to chewing gum compositions containing medicament absorbates of magnesium trisilicate and in particular to medicament adsorbates which employ a magnesium trisilicate having a surface area of at least 400 m$^2$/g with a surface structure having multiple interstitial-flaked spaces.

The use of magnesium trisilicates in the preparation of medicament adsorbates has been taught in the literature as a method to render bitter drug principles tasteless in liquid, tablet and chewable dosage forms which become readily bioavailable when the adsorbate reaches the low pH acid media of the stomach.

U.S. Pat. No. 3,085,942 to Magid discloses the formation of an antitussive composition using dextromethorphan and its acid addition salts adsorbed, in part, on magnesium trisilicate. Magid notes that particle size of the magnesium trisilicate is not critical in preparing the adsorbates and that average particle sizes of about 0.1 to about 150 microns are usable. Magid also notes that when the ingredients are intimately mixed, the bitter taste associated with dextromethorphan is reduced or eliminated. The adsorbate may be mixed with other ingredients to form compressed tablets, candy lozenges, chewing gum tablets and the like.

Most of these products when placed in the mouth and chewed, however, cause release of the medicament drug from the adsorbate resulting in the sensation of off-taste medicine to the user. Efforts therefore have been diverted to the development of products that either reduce the amount of medicament or mask the after-taste, such as by minimizing stimulation of the taste buds. These methods have involved various techniques such as microencapsulation as a method of coating particles or liquid droplets with edible polymeric materials; adsorption onto substrates capable of keeping the drugs adsorbed while in the mouth but releasing them eventually in the stomach or gastrointestinal tract; spray congealing and spray coating involving taste masking of materials with fatty acids or monoglycerides and diglycerides of edible fatty acids; formation of different salts or derivatives by modification of the chemical composition of the drug substance itself.

It would, therefore, be desirable to develop a medicament adsorbate that would enable such products to be made without the bitter after-taste characteristics, that result from incorporating effective amounts of bitter medicaments, and that can be made and used easily without elaborate processing procedures.

Applicants have unexpectedly discovered that use of a particular magnesium trisilicate, rather than conventional magnesium trisilicates broadly, such as described by Magid, results in the formation of an adsorbate having adsorbency potentials greater than commercially available grades of magnesium silicates and achieves optimum medicament taste-masking characteristics while providing rapid bioavailability. In particular, applicants have found that an adsorbate exhibiting unexpected results is only achieved with a magnesium trisilicate having a critical surface area of at least 400 m$^2$/g when the particles of the magnesium trisilicate exhibit a flake-like structure having multiple interstitial spaces.

This particular magnesium trisilicate has been found to be suitable for preparation of tasteless medicament adsorbates. While the invention is not to be limited to theoretical considerations, it is believed that the surface area of the magnesium trisilicate coupled with the flaked-like surface results in an unusual ability to absorb the medicament drug within the channels, convolutions or interstitial spaces of the adsorbate. Once adsorbed within the magnesium trisilicate, the drug is not available for organoleptic taste prior to passage into the digestive tract and subsequent desorption by the gastric juice. This pronounced absorption effect is not found in normal commercially available magnesium trisilicate and appears to be unrelated to particle size.

Accordingly, the applicants have unexpectedly discovered a medicament adsorbate which comprises magnesium trisilicate having a surface area of at least 400 m$^2$/g which has a flake-like structure having multiple interstitial space, containing from about 1% to about 20% by weight of the adsorbate of a medicament drug.

Applicants have also unexpectedly discovered a process for preparing the medicament adsorbate which process involves dissolving the medicament drug in a solvent, admixing magnesium trisilicate having a surface area of at least 400 m$^2$/g which has a flake-like structure with multiple interstitial spaces therewith to prepare a mass having a homogenous consistency to enable the medicament drug to migrate within the magnesium trisilicate interstitial spaces and recovering the medicament adsorbate product.

The medicament adsorbate of the invention may be incorporated into a carrier in the form of a chewing gum.

Referring to the drawings.

Figure 1:
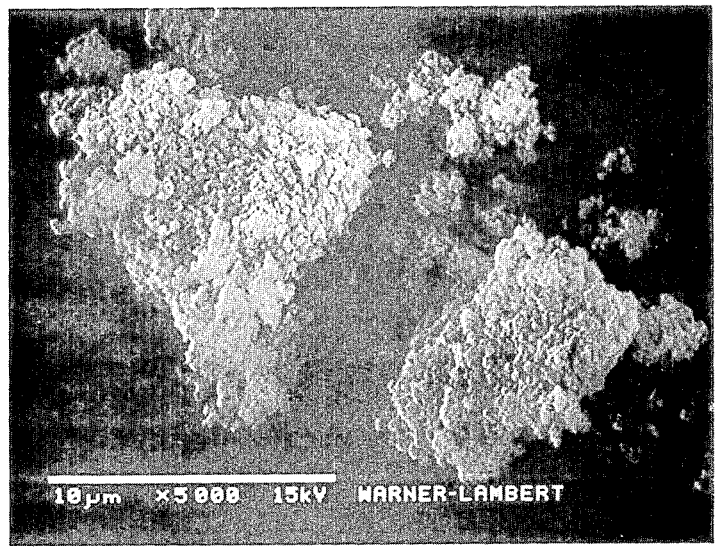
FIG. 1 represents a photomicrograph of magnesium trisilicate of this invention magnified 5000×.

The magnesium trisilicate of the invention is a fine, white odorless powder free from grittiness having a surface area of at least 400 m$^2$/g, and preferably at least 400 m$^2$/g to about 1000 m$^2$/g and most preferably from about 440 to about 600 m$^2$/g which has a flake-like structure with multiple interstitial spaces. It has been unexpectedly found that magnesium trisilicates having these characteristics when used as an adsorbent aid in masking the bitter after-taste associated with various drug compounds.

The instant magnesium trisilicate is distinct from normally available magnesium trisilicates. The term magnesium trisilicate does not have a precise description but approximates the formula $2MgO_3SiO_2 \cdot xH_2O$. The physical texture and absorptive properties of magnesium silicates have been heretofore varied depending predominately upon their mode of preparation. These materials, however, generally possess a water content of 17 to 34%, a minimum of 20% magnesium oxide, a minimum of 45% silicon dioxide, and a ratio of MgO to SiO$_2$ of about 2.10 to about 2.30.

The normal magnesium trisilicate has a surface area of less than 400 m$^2$/g and preferably less than 250m$^2$/g. These materials likewise are globular semispherical structures which are non-flake in appearance and are void of interstitial spaces. Such materials when used as an adsorbent have heretofore failed to effectively mask the bitter taste associated with adsorbed medication while maintaining satisfactory levels of drug activity. It is believed that such conventional materials have heretofore only been able to partially adsorb the medicament as described in U.S. Pat. No. 3,085,942 to Magid on the surface of the magnesium trisilicate. Since the surface of these materials is relatively smooth, efficient adsorption has not been possible and additional aftertaste masking ingredients have been employed.

The method of making the magnesium trisilicates used in this invention is not critical and is not considered a part of this invention. Magnesium trisilicates of this invention are believed to occur naturally or may be prepared by standard techniques well known to the ordinary skilled artisan which would not involve undue experimentation. Such techniques generally use normal reactants, such as sodium silicate and magnesium sulfate which are reacted under heat, the magnesium trisilicate is precipitated and recovered. See for example U.S. Pat. No. 3,272,594.

The medicament drugs used herein may be selected from a wide variety of drugs and their acid addition salts. Both organic and inorganic salts may be used provided the drug maintains its medicament value and is soluble in the solvent. Exemplary acid salts include hydrochlorid, hydrobromide, orthophosphate, benzoate, maleate, tartrate, succinate, citrate, salicylate, sulfate, and acetate.

The weight percent of the drug or its acid addition salt thereof, based on the weight of the adsorbate is preferably from about 1% to about 20%, and most preferably about 5% to about 15%, which amounts will vary depending upon the therapeutic dosage permitted.

Suitable categories of drugs that may be employed in the instant absorbate may vary widely and generally represent any stable adsorbate drug combination. Illustrative categories and specific examples include:

(a) Antitussives, such as dextromethorphan, dextromethorphan hydrobromide, noscapine, carbetapentane citrate, and chlophedianol hydrochloride;

(b) Antihistamines, such as chlorpheniramine maleate, phenindamine tartrate, pyrilamine maleate, doxylamine succinate, phenyltoloxamine citrate, diphenhydramine hydrochloride, promethazine and triprolidine;

(c) Decongestants, such as phenylephrine hydrochloride, phenylpropanolamine hydrochloride, pseudoephedrine hydrochloride, ephedrine and (d) Various Alkaloids, such as codeine phosphate, codeine sulfate and morphine.

(e) Antinauseants, such as dimenhydrinate and meclizine;

(f) Antiasmatics, such as aminophylline, epinephrine, and theophylline;

(g) Analgesics, such as acetaminophen, salicylamide, and phenacetin;

(h) Nutritional supplements, such as niacin, pantothenic acid, vitamin B6, thiamine hydrochloride, riboflavin, potassium iodide, potassium chloride, cupric sulfate, and ferrous sulfate;

(i) Laxatives, such as phenolphthalein, danthron, bisocadyl and pamabrom; and (j) Appetite suppressants, such as caffeine.

These materials may be used alone or in combination on the adsorbate within the ranges specified above.

A particularly effective medicament adsorbate has been prepared using phenylpropanolamine hydrochloride.

The medicament adsorbate of the invention can be prepared by conventional granulation and or slurry techniques. Both processes involve the initial step of dissolving the medicament drug in a suitable inert solvent and then mixing with the magnesium trisilicate. Solvent concentrations may vary widely but are generally from about 15% to about 60% by weight of the total composition. When mixing is performed with low amounts of solvent, for example 15% to about 35% by weight of the total composition, the resulting granulated product is removed and dried to a predetermined moisture content between 5% and 20% by weight of the final composition. When higher solvent concentrations are employed a slurry is formed containing the drug and magnesium trisilicate. Solvent concentrations may range from about 30% to 60% by weight of the total composition for optimum results. The solvent is then removed and the adsorbate recovered and used as a paste or dried to a free flowing powder.

Any solvent may be used in the inventive process to prepare the adsorbate providing it is capable of dissolving the medicament drug. Representative solvents include water; polyhalogenated lower hydrocarbons such as chloroform, methylene chloride; lower alcohols, such as methanol, ethanol, propanol and butanol; and aromatic solvents such as benzene, with water being the preferred solvent.

The medicament adsorbate once prepared may be stored for future use or formulated with conventional additives, that is confectionery carriers, to prepare medicated compositions which offer a variety of textures to suit particular applications. Such compositions may be in the form of a lozenge, tablet, toffee, nougat, chewy candy, chewing gum, and so forth. The confectionery carriers may be selected from a wide range of materials. Without being limited thereto, such materials include bulking agents such as fillers, diluents, binders and adhesives, lubricants, disintegrants, colorants, flavorings, sweeteners and miscellaneous materials such as buffers and adsorbents in order to prepare a particular medicated confectionery composition. The preparation of confectionery and chewing gum products is historically well known and has changed very little over the years.

Lozenges are flavored medicated dosage forms intended to be sucked and held in the mouth. They may be in the form of various shapes, the most common being flat, circular, octagonal and biconvex forms. The lozenge bases are generally in two forms, hard, boiled candy lozenges and compressed tablet lozenges.

The hard boiled candy lozenges are prepared from a mixture of sugar and other carbohydrates that are kept in an amorphous or glassy condition. This form can be considered a solid syrup of sugars generally having from 0.5 to 1.5% moisture. Such materials normally contain up to 92% corn syrup, up to 55% sugar and from 0.1% to 5.0% water. The syrup component generally is prepared from corn syrups high in fructose, but may include other materials. Further ingredients such as flavorings, sweeteners, acidulents, colorants and so forth may also be added.

Boiled candy lozenges may also be prepared from non-fermentable sugars such as sorbitol, mannitol, and hydrogenated corn syrup. A typical hydrogenated corn syrup is lycasin. The candy lozenges may contain up to about 95% sorbitol, a mixture of sorbitol and mannitol at a ratio of about 9.5 to 0.5 up to about 7.5 to 2.5 and hydrogenated corn syrup up to about 55% of the syrup component.

In contrast, compressed tablet lozenges contain particular materials and are formed into structures under pressure. They generally contain sugars in amounts up to 95% and typical tablet excipients such as binders and lubricants as well as flavors, colorants and so forth.

The lozenges may be made of soft confectionary materials such as those contained in nougat. These materials contain two primary components, namely a high boiling syrup such as corn syrup or the like, and a relatively light textured frappe, generally prepared from gelatin, egg albumen, milk proteins such as casein, and vegetable proteins such as soy protein, and the like. The frappe is generally relatively light, and may, for example, range in density from about 0.5 to about 0.7g/cc.

By comparison, the high boiling syrup, or "bob syrup", is relatively viscous and possesses a higher density, and frequently contains a substantial amount of sugar. Conventionally, the final nougat composition is prepared by the addition of the "bob syrup" to the frappe under agitation, to form the basic nougat mixture. Further ingredients such as flavorings, oils, additional sugar and the like may be added thereafter also under agitation. A general discussion of the composition and preparation of nougat confections may be found in B.W. Minifie, *CHOCOLATE, COCOA AND CONFECTIONERY: Science and Technology*, 2nd edition, AVI Publishing Co., Inc., Westport, Connecticut, (1980), at pages 424–425.

Tablets of this invention may also be in chewable form. This form is particularly advantageous because of convenience and patient acceptance and rapid onset of bioactivity. To achieve acceptable stability and quality as well as good taste and mouth feel several considerations are important, namely amount of active substance per tablet, flavor, compressibility and organoleptic properties of the drug.

The preparation of chewable medicated candy is prepared by procedures similar to those used to make soft confectionary. This procedure generally involves the formation of a boiled sugar-corn syrup blend to which is added a frappe mixture. The boiled sugar-corn syrup blend may be prepared from sugar and corn syrup blended in parts by weight ratio of 90 to 10:10 to 90. This blend is heated to temperatures above 250° F. to remove water and to form a molten mass. The frappe is generally prepared from gelatin, egg albumen, milk proteins such as casein, and vegetable proteins such as soy protein, and the like which are added to a gelatin solution and rapidly mixed at ambient temperature to form an aerated sponge like mass. The frappe is then added to the molten candy base and mixed until homogenous at temperatures between 150° F. and 250° F. The medicament adsorbate can then be added as the temperature of the mix is lowered to around 150° F. to 200° F. whereupon additional ingredients are added such as flavors, and colorants. The formulation is further cooled and formed to pieces of desired dimensions.

A general discussion of the lozenge and chewable tablet forms of confectionery may be found in H.A. Lieberman and L. Lachman, *Pharmaceutical Dosage Forms: Tablets* Volume 1, Marcel Dekker, Inc., New York, N.Y. at pages 289 to 466, incorporated herein by reference.

With regard to the chewing gum formulation in particular, the amount of gum base employed will vary greatly depending on various factors such as the type of base used, consistency desired and other components used to make the final product. In general, amounts of about 5% to about 45% by weight of the final chewing gum composition are acceptable for use in chewing gum compositions with preferred amounts of about 15% to about 25% by weight. The gum base may be any water-insoluble gum base well known in the art. Illustrative examples of suitable polymers in gum bases include both natural and synthetic elastomers and rubbers. For example, those polymers which are suitable in gum bases, include, without limitation, substances of vegetable origin such as chicle, jelutong, gutta percha and crown gum. Synthetic elastomers such as butadiene-styrene copolymers, isobutylene-isoprene copolymers, polyethylene, polyisobutylene and polyvinylacetate and mixtures thereof, are particularly useful.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of $\alpha$-pinene or $\beta$-pinene; terpene resins including polyterpene and mixtures thereof. The solvent may be employed in an amount ranging from about 10% to about 75% and preferable about 45% to about 70% by weight to the gum base.

A variety of traditional ingredients such as plasticizers or softeners such as lanolin, stearic acid, sodium stearate, potassium stearate, glyceryl triacetate, glycerine and the like for example, natural waxes, petroleum waxes, such as polyurethene waxes, paraffin waxes and microcrystalline waxes may also be incorporated into the gum base to obtain a variety of desirble textures and consistency properties. These individual additional materials are generally employed in amounts of up to about 30% by weight and preferably in amounts of from about 3% to about 20% by weight of the final gum base composition.

The chewing gum composition may additionally include the conventional additives of flavoring agents, coloring agents such as titanium dioxide; emulsifiers such as lecithin and glyceryl monostearate; and additional fillers such as aluminum hydroxide, alumina, aluminum silicates, calcium carbonate, and talc and combinations thereof. These fillers may also be used in the gum base in various amounts. Preferably the amount of fillers when used will vary from about 4% to about 30% by weight of the final chewing gum.

In the instance where auxiliary sweeteners are utilized, the present invention contemplates the inclusion of those sweeteners well known in the art, including both natural and artificial sweeteners. Thus, additional sweeteners may be chosen from the following non-limiting list:

A. Water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol and mixtures thereof.

B. Water-soluble artificial sweeteners such as the soluble saccharin salts, i.e., sodium, or calcium saccharin salts, cyclamate salts, acesulfam-K and the like, and the free acid form of saccharin.

C. Dipeptide based sweeteners such as L-aspartyl-phenylalanine methyl ester and materials described in U.S. Pat. No. 3,492,131 and the like.

In general, the amount of sweetener will vary with the desired amount of sweeteners selected for a particular chewing gum. This amount will normally be 0.001% to about 90% by weight when using an easily extractable sweetener. The water-soluble sweeteners described in category A above, are preferably used in amounts of about 25% to about 75% by weight, and most preferably from about 50% to about 65% by weight of the final chewing gum composition. In contrast, the artificial sweeteners described in categories B and C are used in amounts of about 0.005% to about 5.0% and most preferably about 0.05 to about 2.5% by weight of the final chewing gum composition. These amounts are ordinarily necessary to achieve a desired level of sweetness independent from the flavor level achieved from flavor oils. While water may be added independently with dry sweeteners, it will generally be added as part of a corn syrup or corn syrup mixture.

Suitable flavorings include both natural and artificial flavors, and mints such as peppermint, menthol, artificial vanilla, cinnamon, various fruit flavors, both individual and mixed, and the like are contemplated. The flavorings are generally utilized in amounts that will vary depending upon the individual flavor, and may, for example, range in amounts of about 0.5% to about 3% by weight of the final composition weight.

The colorants useful in the present invention, include the pigments such as titanium dioxide, that may be incorporated in amounts of up to about 1% by weight, and preferably up to about 0.6% by weight. Also, the colorants may include other dies suitable for food, drug and cosmetic applications, and known as F.D. & C. dyes and the like. The materials acceptable for the foregoing spectrum of use are preferably water-soluble. Illustrative examples include indigoid die, known as F.D. & C. Blue No. 2, which is the disodium salt of 5,5'-indigotin-disulfonic acid. Similarly, the dye known as F.D. & C. Green No. 1, comprises a triphenylmethane dye and is the monosodium salt of 4-[4-Nethyl-p-sulfobenzylamino)diphenylmethylene]-[1-(N-ethyl-N-p-sulfoniumbenzyl)- 2,5-cyclohexadienimine]. A full recitation of all F.D. & C. and D. & C. and their corresponding chemical structures may be found in the Kirk-Othmer Encyclopedia of Chemical Technology, in volume 5, at Pages 857–884, which text is accordingly incorporated herein by reference.

Suitable oils and fats that are useable would include partially hydrogenated vegetable or animal fats, such as coconut oil, palm kernel oil, beef tallow, lard, and the like. These ingredients are generally utilized in amounts with respect to the comestible product of up to about 7.0% by weight, and preferably up to about 3.5% by weight of the final product.

The medicated adsorbate can be incorporated into sugar or sugarless chewing gum combinations which can be made into a variety of products, e.g., stick, slab, chunk, ball, rope, shredded tablet and/or center filled.

It is generally accepted that as the required amount of active substance per structure gets smaller and/or less bad tasting, the task at arriving at an acceptable formulation becomes easier due to the greater number of formulations available. Alternately, extremely bad-tasting and/or high-dose drugs are difficult to formulate into medicament/chewable tablets. The medicament adsorbates of this invention overcome these difficulties.

The quantity of adsorbate used may vary widely depending upon the particular medicament drug dosage. Amounts of medicament of about 1.0 to about 400 mg per medicated dosage are useable dependant upon the particular medicament. Naturally amounts of medicament adsorbate used will be higher depending on the therapeutic dosage required and amount of medicament adsorbed on the substrate. Illustrative examples are described below.

The usual dosage of phenylpropanolamine hydrochloride is between 10 and 50 mg per tablet. Incorporation of the adsorbate into, for example, a candy base is not difficult because of its melting point and solvent solubility. It is compatible with most flavors and is stable over a wide pH range. The phenylpropanolamine hydrochloride when added as the medicament adsorbate avoids its bitter taste and flavoring difficulty.

The usual dosage of ephedrine hydrochloride is about 20 to 50 mg per tablet. The formulation is not difficult to flavor because of the absence of medicament after-taste. The usual dosage of pyrilamine maleate is 25 to 50 mg per tablet. The usual dosage of pseudophedrine hydrochloride is 15 to 60 mg per tablet. Naturally, the exact amount used will vary with the particular application and drug.

The medicament adsorbate is generally present with the pharmaceutically acceptable carrier in an amount of from about 1% to about 60% by weight of the final composition. The exact amount will be dependent upon the particular medicament and dosage required.

The present invention is further illustrated by the following examples. All parts and percentages in the examples and throughout the specification and claims are by weight unless otherwise indicated.

EXAMPLE 1

(Inventive Runs 1 and 2)

This Example demonstrates a method for preparing a dextromethorphan hydrobromide adsorbate.

To 30 grams water is mixed 6 grams dextromethorphan hydrobromide, at a water temperature around 90° C., until the drug was in solution. The solution was added to 60 grams magnesium trisilicate having a mean specific surface area of 506.1 m2/g and mixed until a homogenous dispersion resulted, approximately 30 minutes. The mix was then oven dried at 70° C. until a moisture content of below 15% was obtained. The product was then milled to prepare a white free-flowing powder containing 10% by weight dextromethorphan hydrobromide.

An organoleptic evaluation test was performed on the product to determine the presence or absence of bitterness. The instant product did not exhibit any bitterness or off taste when tested by a human panel of experts.

The specific mean surface area of the materials were measured using the Quantasorb Sorption System (Quantachrome Corporation, N.Y.)

The results are set forth in Table I.

FIG. 1 represents a photomicrograph of magnesium trisilicate of this invention magnified 5000×. The Figure depicted shows a flake-like structure having extensive interstitial spaces. The flake-like character is evident throughout the entire structure and does not merely appear on the surface. No agglomeration or other spherical particles are noted.

Figure 2:
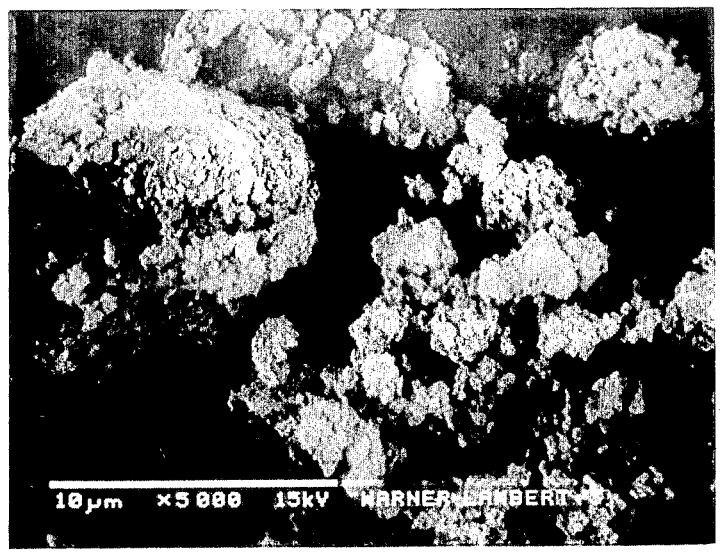
FIG. 2 represents a photomicrograph of a dextromethorphan HBr adsorbate of this invention magnified 5000×.

FIG. 2 represents a photomicrograph of the dextromethorphan HBr adsorbate prepared in this inventive example magnified 5000×. The Figure depicts a flake-like structure having extensive interstitial spaces. The flake-like character is evident throughout the structure and does not merely appear on the surface. No agglomerates or other spherical particles are noted.

EXAMPLE 2

(Comparative Runs A and B)

This Example demonstrates a dextromethorphan hydrobromide adsorbate believed to be prepared by the process of Example 1 of U.S. Pat. No. 3,085,942 to Hoffman-La Roche Inc. These materials are at least 10 years old. The process used broadly involved forming a mixture of dextromethorphan hydrobromide and magnesium trisilicate having an average particle size of 5-microns by dissolving the dextromethorphan hydrobromide in distilled water (80° C.), and then pouring the resulting solution onto the magnesium trisilicate. The resulting mixture is then thoroughly mixed by stirring to form a slurry. The solvent is then removed by spray-drying. A white free-flowing powder is obtained.

An organoleptic evaluation test was performed on the adsorbate product to determine the presence or absence of bitterness. The product demonstrated acceptable characteristics in that it reduced the bitterness of the drug.

The mean specific surface area was measured as in Example 1, Run 1 with results set forth in Table I.

Figure 3:
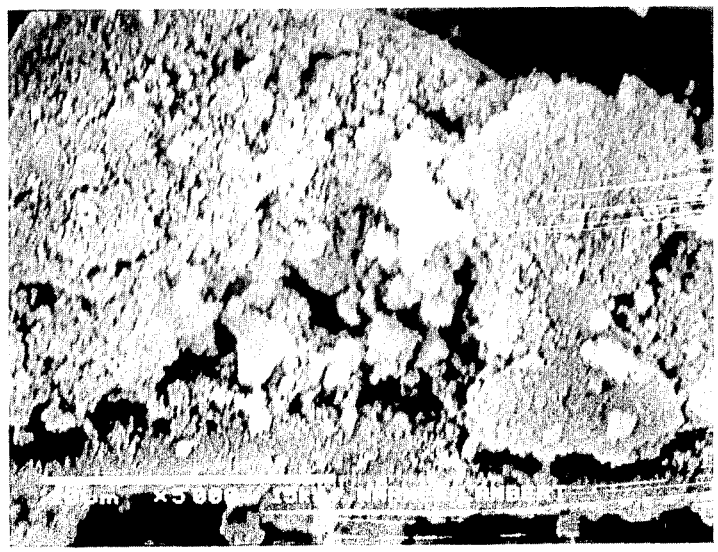
FIG. 3 represents a photomicrograph of a normal magnesium trisilicate magnified 5000×.

FIG. 3 represents a photomicrograph of the old magnesium trisilicate magnified 5000×. The Figure depicts an agglomerated product, with some interstitial spaces but absence of flake-like character throughout its structure.

Figure 4:
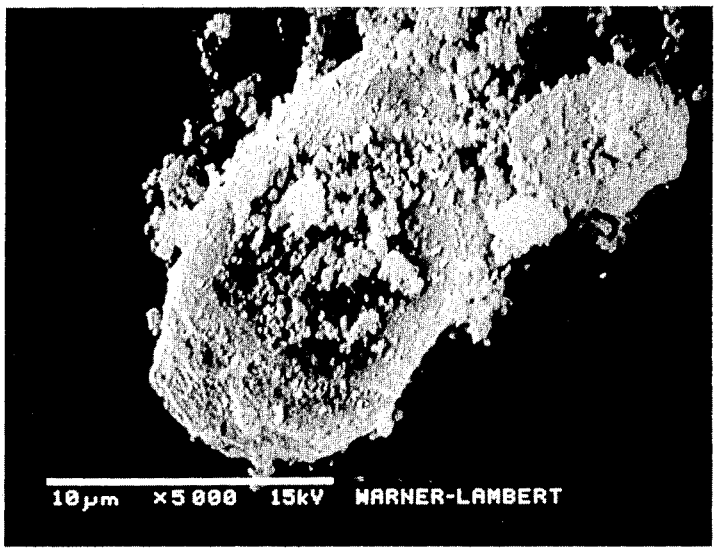
FIG. 4 represents a photomicrograph of a normal dextromethorphan HBr adsorbate magnified 5000×.

FIG. 4 represents a photomicrograph of the old dextromethorphan HBr adsorbate magnified 5000×. The Figure depicts a smooth surfaced particle lacking interstitial spaces and flaked structure.

TABLE I

| Run | Material | Mean Specific Surface Area ($M^2/g$) | Structure |
| --- | --- | --- | --- |
| Inventive 1 | Magnesium trisilicate | 506.1 | Flaked (FIG. 1) |
| Comparative A | Old magnesium trisilicate | 415.1 | Agglomerated (FIG. 3) |
| Inventive 2 | Dextromethorphan HBr—10% adsorbate | 209.8 | Flaked (FIG. 2) |
| Comparative B | Old dextromethorphan HBr—10% adsorbate | 66.35 | Smooth (FIG. 4) |

EXAMPLE 3

Inventive Runs 3, 4, 5 and 6

Comparative Runs C, D, E and F

This Example compares the properties derived from various dextromethorphan HBr adsorbates prepared by the process of Example 1 using different magnesium trisilicates from different commercial sources.

The results are set forth in Table II.

TABLE II

| | | Magnesium Trisilicate | |
| --- | --- | --- | --- |
| Run | Adsorbate Taste | Mean Specific Surface Area ($m^2/g$) | Structure |
| Inventive 3 | Good | 441.8 | Flaked |
| Inventive 4 | Good | 460.4 | Flaked |
| Inventive 5 | Good | 564.2 | Flaked |
| Inventive 6 | Good | — | Flaked |
| Comparative C | Bitter | 181.8 | Smooth Surface |
| Comparative D | Bitter | 240.8 | Smooth Surface |
| Comparative E | Bitter | — | — |
| Comparative F | Bitter | — | — |

EXAMPLE 4

(Inventive Run 7)

This Example demonstrates a method for preparing a carbetapentane citrate adsorbate.

To 400 grams water is mixed 75 grams carbetapentane citrate, at a water temperature around 90° C., until the drug was in solution. The solution was added to 1,000 grams magnesium trisilicate having a mean specific surface area of at least 400 $m^2/g$ and mixed until a homogenous dispersion resulted, approximately 30 minutes. The mix was then oven dried at 75° C. until a moisture content of below 15% was obtained. The product was then milled to prepare a white free-flowing powder containing 7.5% by weight carbetapentane citrate.

An organoleptic evaluation test was performed on the product to determine the presence or absence of bitterness. The instant product did not exhibit objectionable bitterness or off taste when tested by a human panel of experts.

EXAMPLE 5

(Inventive Run 8)

This Example demonstrates a method for preparing a chlophedianol adsorbate.

To 400 grams water and 347.6 grams of 1N hydrocloric acid is mixed 100.8 grams chlophedianol, at a water temperature around 90° C., until the drug was in solution. The solution was added to 1,000 grams magnesium trisilicate having a mean specific surface area of at least 400 $m^2/g$ and mixed until a homogenous dispersion resulted, approximately 30 minutes. The mix was then oven dried at 75° C. until a moisture content of below 15% was obtained. The product was then milled to prepare a white free-flowing powder containing 10% by weight chlophedianol.

An organoleptic evaluation test was performed on the product to determine the presence or absence of bitterness. The instant product did not exhibit objectionable bitterness or off taste when tested by a human panel of experts.

EXAMPLE 6

(Inventive Run 9)

This Example demonstrates a method for preparing a chlophedianol/ephedrine hydrochloride adsorbate.

To 400 grams water and 260.69 grams of 1N hydrochloric acid is mixed 75.6 grams chlophedianol and 30 grams ephedrine hydrochloride, at a water temperature around 80° C., until the drugs were in solution. The solution was added to 1,000 grams magnesium trisilicate having a mean specific surface area of at least 400 $m^2/g$ and mixed until a homogenous dispersion resulted, approximately 30 minutes. The mix was then oven dried at 65° C. until a moisture content of below 15% was obtained. The product was then milled to prepare a white free-flowing powder containing 7.56% by weight chlophedianol and 3% by weight ephedrine.

An organoleptic evaluation test was performed on the product to determine the presence or absence of bitterness. The instant product did not exhibit objectional bitterness or off taste when tested by a human panel of experts.

EXAMPLE 7

(Inventive Run 10)

This example demonstrates a method for preparing a pyrilamine maleate adsorbate.

To 700 grams water is mixed 100 grams pyrilamine, maleate at a water temperature around 90° C., until the drug was in solution. The solution was added to 1,000 grams magnesium trisilicate having a mean specific surface area of at least 400 $m^2/g$ and mixed until a homogeneous dispersion resulted, approximately 30 minutes. The mix was then oven dried at 85° C. until a moisture content of below 15% was obtained. The product was then milled to prepare a white free-flowing powder containing 10% by weight pyrilamine maleate.

An organoleptic evaluation test was performed on the product to determine the presence or absence of bitterness. The instant product did not exhibit objectional bitterness or off taste when tested by a human panel of experts.

EXAMPLE 8

(Inventive Run 11)

This example demonstrates a method for preparing a diphenhydramine hydrochloride adsorbate.

To 873 grams water is mixed 99.4 grams diphenhydramine hydrochloride, at a water temperature around 90° C., until the drug was in solution. The solution was added to 1,000 grams magnesium trisilicate having a mean specific surface area of at least 400 $m^2/g$ and mixed until a homogeneous dispersion resulted, approximately 30 minutes. The mix was then oven dried at 75° C. until a moisture content of below 15% was obtained. The product was then milled to prepare a white free-flowing powder containing 9.94% by weight diphenhydramine hydrochloride.

An organoleptic evaluation test was performed on the product to determine the presence or absence of bitterness. The instant product did not exhibit objectional bitterness or off taste when tested by a human panel of experts.

EXAMPLE 9

(Inventive Run 12)

This example demonstrates a method for preparing a phenyltoloxamine citrate adsorbate.

To 700 grams water is mixed 100 grams phenyltoloxamine citrate, at a water temperature around 90° C., until the drug was in solution. The solution was added to 1,000 grams magnesium trisilicate having a mean specific surface area of at least 400 $m^2/g$ and mixed until a homogeneous dispersion resulted, approximately 30 minutes. The mix was then oven dried at 85° C. until a moisture content of below 15% was obtained. The product was then milled to prepare a white free-flowing powder containing 10% by weight phenyltoloxamine citrate.

An organoleptic evaluation test was performed on the product to determine the presence or absence of bitterness. The instant product did not exhibit objectional bitterness or off taste when tested by a human panel of experts.

EXAMPLE 10

(Inventive Run 13)

This example demonstrates a method for preparing a phenindamine tartrate adsorbate.

To 700 grams water is mixed 100 grams phenindamine tartrate, at a water temperature around 90° C., until the drug was in solution. The solution was added to 1,000 grams magnesium trisilicate having a mean specific surface area of at least 400 $m^2/g$ and mixed until a homogeneous dispersion resulted, approximately 30 minutes. The mix was then oven dried at 85° C. until a moisture content of below 15% was obtained. The product was then milled to prepare a white free-flowing powder containing 10% by weight phenindamine tartrate.

An organoleptic evaluation test was performed on the product to determine the presence or absence of bitterness. The instant product did not exhibit objectional bitterness or off taste when tested by a human panel of experts.

The invention being thus described, it will be obvious that the same may be varied in many ways. Such variations are not to be regarded as a departure from the spirit and scope of the invention and all such modifications are intended to be included within the scope of the following claims.

EXAMPLE 11

(Inventive Run 14)

This example demonstrates a method for preparing a phenylpropanolamine hydrochloride adsorbate.

To 700 grams water is mixed 100 grams phenylpropanolamine hydrochloride, at a water temperature around 90° C., until the drug was in solution. The solution was added to 1,000 grams magnesium trisilicate having a mean specific surface area of at least 400 $m^2/g$ and mixed until a homogeneous dispersion resulted, approximately 30 minutes. The mix was then oven dried at 85° C. until a moisture content of below 15% was obtained. The product was then milled to prepare a white free-flowing powder containing 10% by weight phenylpropanolamine hydrochloride.

An organoleptic evaluation test was performed on the product to determine the presence or absence of bitterness. The instant product did not exhibit objectional bitterness or off taste when tested by a human panel of experts.

EXAMPLE 12

(Inventive Run 15)

This Example demonstrates a method for preparing a codeine phosphate adsorbate.

To 250 grams water is mixed 49.5 grams codeine phosphate, at a water temperature around 90° C., until the drug was in solution. The solution was added to 495 grams magnesium trisilicate having a mean specific surface area of at least 400 m$^2$/g and mixed until a homogeneous dispersion resulted, approximately 30 minutes. The mix was then oven dried at 80° C. until a moisture content of below 15% was obtained. The product was then milled to prepare a white free-flowing powder containing 10% by weight codeine phosphate.

An organoleptic evaluation test was performed on the product to determine the presence or absence of bitterness. The instant product did not exhibit objectional bitterness or off taste when tested by a human panel of experts.

The invention being thus described, it will be obvious that the same may be varied in many ways. Such variations are not to be regarded as a departure from the spirit and scope of the invention and all such modifications are intended to be included within the scope of the following claims.

EXAMPLE 13

(Inventive Run 16)

This Example demonstrates a method for preparing a dimenhydrinate adsorbate.

To 3,000 grams water is mixed 900 grams dimenhydrinate, at a water temperature around 90° C., until the drug was in solution. The solution was added to 4,000 grams magnesium trisilicate having a mean specific surface area of at least 400 m$^2$/g and mixed until a homogeneous dispersion resulted, approximately 30 minutes. The mix was then oven dried at 75° C. until a moisture content of below 15% was obtained. The product was then milled to prepare a white free-flowing powder containing 22.5% by weight dimenhydrinate.

An organoleptic evaluation test was performed on the product to determine the presence or absence of bitterness. The instant product did not exhibit objectional bitterness or off taste when tested by a human panel of experts.

The invention being thus described, it will be obvious that the same may be varied in many ways. Such variations are not to be regarded as a departure from the spirit and scope of the invention and all such modifications are intended to be included within the scope of the following claims.

EXAMPLE 14

(Inventive Run 17)

This Example demonstrates a method for preparing a acetaminophen adsorbate.

To 300 grams water and 450 grams of alcohol USP is mixed 250 grams acetaminophen, at a temperature around 40° C., until the drug was in solution. The solution was added to 1,000 grams magnesium trisilicate having a mean specific surface area of at least 400 m$^2$/g and mixed until a homogeneous dispersion resulted, approximately 30 minutes. The mix was then oven dried at 85° C. until a moisture content of below 15% was obtained. The product was then milled to prepare a white free-flowing powder containing 25% by weight acetaminophen.

An organoleptic evaluation test was performed on the product to determine the presence or absence of bitterness. The instant product did not exhibit objectional bitterness or off taste when tested by a human panel of experts.

The invention being thus described, it will be obvious that the same may be varied in many ways. Such variations are not to be regarded as a departure from the spirit and scope of the invention and all such modifications are intended to be included within the scope of the following claims.

EXAMPLE 15

(Inventive Run 18)

This Example demonstrates a method for preparing a caffeine adsorbate.

To 700 grams water is mixed 200 grams caffeine, at a water temperature around 90° C., until the drug was in solution. The solution was added to 1,000 grams magnesium trisilicate having a mean specific surface area of at least 400 m$^2$/g and mixed until a homogeneous dispersion resulted, approximately 30 minutes. The mix was then oven dried at 85° C. until a moisture content of below 15% was obtained. The product was then milled to prepare a white free-flowing powder containing 20% by weight caffeine.

An organoleptic evaluation test was performed on the product to determine the presence or absence of bitterness. The instant product did not exhibit objectional bitterness or off taste when tested by a human panel of experts.

The invention being thus described, it will be obvious that the same may be varied in many ways. Such variations are not to be regarded as a departure from the spirit and scope of the invention and all such modifications are intended to be included within the scope of the following claims.

EXAMPLE 16

(Inventive Run 18)

This Example demonstrates a method for preparing a theophylline adsorbate.

To 700 grams water is mixed 100 grams theophylline, at a water temperature around 98° C., until the drug was in solution. The solution was added to 1,000 grams magnesium trisilicate having a mean specific surface area of at least 400 m$^2$/g and mixed until a homogeneous dispersion resulted, approximately 30 minutes. The mix was then oven dried at 85° C. until a moisture content of below 15% was obtained. The product was then milled to prepare a white free-flowing powder containing 10% by weight theophylline.

An organoleptic evaluation test was performed on the product to determine the presence or absence of bitterness. The instant product did not exhibit objectionable bitterness or off taste when tested by a human panel of experts.

The invention being thus described, it will be obvious that the same may be varied in many ways. Such variations are not to be regarded as a departure from the spirit and scope of the invention and all such modifications are intended to be included within the scope of the following claims.

EXAMPLE 17

(Inventive Runs 19 and 20)

This example demonstrates a method for preparing an appetite suppressant chewing gum formulation using an adsorbate prepared with caffeine.

The following ingredients are mixed in the order indicated:

| Ingredient | % by Weight of Chewing Gum Composition | |
| --- | --- | --- |
| | Run 19 | Run 20 |
| Gum base | 24.0 | 24.0 |
| Sugar | — | 45.0 |
| Sorbitol | 44.9 | — |
| Caffeine-20% adsorbate (150 mg drug/dose) | 25.0 | 25.0 |
| Glycerin | 4.2 | 4.2 |
| Saccharin | 0.1 | — |
| Lecithin | 0.3 | 0.3 |
| Flavor | 1.5 | 1.5 |

Process for Inventive Run 19

Heat the gum base to about 95° C. Admix the sorbitol, caffeine adsorbate and glycerin with the gum base to form a uniform mixture. With continued mixing add the saccharin, flavor and lecithin to form a uniform mixture. Recover the product and form it into sticks of chewing gum weighing about 3 grams each.

Process for Inventive Run 20

Follow the same procedure as in Inventive Run 19 replacing the sorbitol with sugar and deleting the saccharin.

The invention being thus described, it will be obvious that the same may be varied in many ways. Such variations are not to be regarded as a departure from the spirit and scope of the invention and all such modifications are intended to be included within the scope of the following claims.

What is claimed is:

1. A chewing gum composition which comprises a chewing gum and from about 1% to about 60% by weight of the final composition of a medicament absorbate containing magnesium trisilicate having a surface area of at least 400 $m^2/g$ and having a flake-like structure with multiple interstitial spaces and from about 1% to about 20% by weight of the absorbate of a medicament drug wherein the medicament drug is selected from the group consisting of antitusussives, antihistamines, decongestants, alkaloids, antinauseants, antiasmatics, analgesics, nutritional supplements, laxatives, appetite suppressants and mixtures thereof.

* * * * *

UNITED STATES PATENT AND TRADEMARK OFFICE
CERTIFICATE OF CORRECTION

PATENT NO. : 4,647,450

DATED : Mar. 3, 1987

INVENTOR(S) : David Peters, et al.

It is certified that error appears in the above-identified patent and that said Letters Patent is hereby corrected as shown below:

Column 16, line 21 delete "antitusussives" and insert therefor --antitussives--.

Signed and Sealed this

Twenty-fifth Day of August, 1987

Attest:

DONALD J. QUIGG

Attesting Officer     Commissioner of Patents and Trademarks